United States Patent
Dufrancatel et al.

(10) Patent No.: US 9,475,758 B2
(45) Date of Patent: Oct. 25, 2016

(54) COMPOUNDS, METHOD FOR PREPARATION THEREOF AND USE THEREOF FOR PREPARING POLYMERS USEFUL FOR INCREASING HEAT RESISTANCE OF POLYMERIC COMPOSITIONS

(75) Inventors: Laurence Dufrancatel, Herblay (FR); Pauline Kannengiesser, Pontoise (FR); Gregory Yhuel, Cergy (FR); Sinisa Marinkovic, Avancon (FR); Boris Estrine, Nanteuil la Foret (FR); Patrice Dole, Journans (FR)

(73) Assignee: Faurecia Interieur Industrie, Nanterre (FR)

( * ) Notice: Subject to any disclaimer, the term of this patent is extended or adjusted under 35 U.S.C. 154(b) by 215 days.

(21) Appl. No.: 13/884,540

(22) PCT Filed: Nov. 9, 2011

(86) PCT No.: PCT/EP2011/069733
§ 371 (c)(1),
(2), (4) Date: Aug. 20, 2013

(87) PCT Pub. No.: WO2012/062799
PCT Pub. Date: May 18, 2012

(65) Prior Publication Data
US 2014/0005351 A1    Jan. 2, 2014

(30) Foreign Application Priority Data
Nov. 9, 2010  (FR) .................................. 10 59256

(51) Int. Cl.
| | | |
|---|---|---|
| C08F 283/00 | (2006.01) |
| C07C 235/74 | (2006.01) |
| C07C 233/36 | (2006.01) |
| C08G 63/685 | (2006.01) |
| C08G 69/44 | (2006.01) |
| C08L 67/02 | (2006.01) |
| C08L 77/12 | (2006.01) |
| C07C 231/12 | (2006.01) |

(52) U.S. Cl.
CPC ........... *C07C 235/74* (2013.01); *C07C 231/12* (2013.01); *C07C 233/36* (2013.01); *C08G 63/6856* (2013.01); *C08G 69/44* (2013.01); *C08L 67/02* (2013.01); *C08L 77/12* (2013.01)

(58) Field of Classification Search
CPC ...................................................... C08L 77/12
USPC ................. 525/240; 528/335, 339
See application file for complete search history.

(56) References Cited

U.S. PATENT DOCUMENTS

| | | | |
|---|---|---|---|
| 5,644,020 A | 7/1997 | Timmermann et al. | |
| 6,172,167 B1 * | 1/2001 | Stapert et al. ................ | 525/420 |
| 2004/0171518 A1 | 9/2004 | Van Antwerp et al. | |

FOREIGN PATENT DOCUMENTS

| | | |
|---|---|---|
| CN | 1403872 A | 3/2003 |
| GB | 2074564 A | 11/1981 |
| JP | 60-049029 A | 3/1985 |
| JP | 60-063225 A | 4/1985 |
| JP | 63277238 A | 11/1988 |

OTHER PUBLICATIONS

USPTO structure seach, May 2015.*
Arvanitoyannis et al Synthesis and study of novel biodegradable oligo(ester amide)s based on sebacic acid, octadecanedioic acid, 1 ,6-hexanediamine and E-caprolactone: 2, Polymer, vol. 36 No. 4. pp. 857-866. 1995), Apr. 1995.*
International Search Report for application No. PCT/EP2011/069733, dated Dec. 14, 2011, 5 pages.
S. Pivsa-Art et al.: "Biodegradability study of copolyesteramides based on diacid chlorides, diamines, and diols", Journal of Applied Science, vol. 85, 2002, pp. 774-784, XP002664975, John Wiley & Sons, Inc., ISSN: 0021-8995; Scheme I; p. 774; table II.
Alena Braunova et al.: "Degradation behavior of poly (ethyleneglycol) diblock and multiblock polymers with hydrolytically degradable ester linkages", Collection of Czechoslovak Chemical Communications, vol. 69, No. 8, 2004, pp. 1643-1656, XP002637664, Institute of Organic Chemistry & Biochemistry; ISSN 0010-0765, p. 1650, line 1-line 10.
Japanese Office action corresponding to application No. 2013-538178, mailed Jun. 23, 2015, 3 pages.
Pieter J. Dijkstra, Henk R. Stapert, Jan Feijen, Synthesis of aliphatic poly(ester-amide)s containing uniform bisamide-biester blocks, Macromol. Symp., 2000, pp. 127-137, vol. 152, WILEY-VCH Verlag GmbH, Weinheim, Germany.
Thomas Fey, Markus Holscher, Helmut Keul, Hartwig Hocker, Alternating poly(ester amide)s from succinic anhydride and α,ω-amino alcohols: synthesis and thermal characterization, Polymer International, Sep. 3, 2003, pp. 1625-1632, vol. 52, Society of Chemical Industry, published online.

* cited by examiner

Primary Examiner — Gregory Listvoyb
(74) Attorney, Agent, or Firm — Reising Ethington P.C.

(57) ABSTRACT

The invention relates to a compound of the following formula (I): to its method for making it and to its uses for preparing a polymer useful for increasing the heat resistance of polymeric compositions.

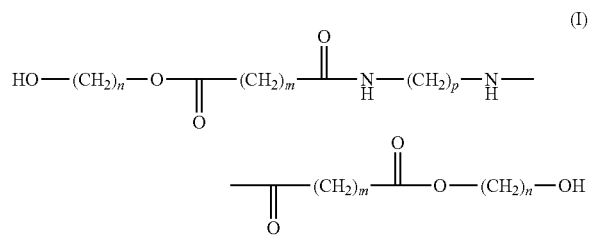

18 Claims, No Drawings

COMPOUNDS, METHOD FOR PREPARATION THEREOF AND USE THEREOF FOR PREPARING POLYMERS USEFUL FOR INCREASING HEAT RESISTANCE OF POLYMERIC COMPOSITIONS

TECHNICAL FIELD

The present invention relates to the preparation of polymeric compositions useful for preparing plastic articles, notably vehicle parts, such as automobile parts.

BACKGROUND

Certain polymeric compositions do not have sufficient heat resistance in order to allow their use as plastic articles, notably as vehicle parts. In particular, polymeric compositions used as materials in the automotive field, notably inside cars behind the glazed surfaces, should be able to withstand temperatures above 120° C.

Various methods have been described for improving heat resistance of polymers, notably incorporation of rigid functions into the polymer, for example aromatic rings. However, a large molar proportion of aromatic rings (of more than 25% molar) has to be incorporated into the polymer in order to observe an improvement in the heat resistance of the polymer, which is costly and which changes the behavior of the polymer: the crystallization kinetics become much lower. The polymer is amorphous in the injection process and its heat resistance is too low for making plastic articles, notably vehicle parts. Further because of the presence of these aromatic rings, the modified polymers cannot stem from renewable resources.

Poly(esteramide) polymers advantageously have interesting thermal, mechanical and biodegradability properties and are therefore materials suitable for preparing plastic articles which may withstand temperatures above 120° C. Methods for preparing these poly(esteramide) polymers by polymerization have been described in the literature.

However, it was observed that these methods only operate with certain monomers used as a starting product and not with other ones. In particular, attempts for obtaining poly(esteramide) polymers from glutaric and succinic acid (or from their derivatives, notably the corresponding anhydrides) have failed, since these polymers form highly stable cyclic imides preventing polymerization. For example, the method applied by Thomas Fey et al. (Polym. Int. 52, 1625-1632, 2003) does not operate with N-(hydroxyalkyl) imides obtained from succinic anhydride, as starting monomers. Also, Pieter J. Dijkstra (Macromol. Symp. 152, 127-137, 2000) reports an unsuccessful polymerization attempt from dimethyl 6,11-diaza-5,12-dioxo-1,16-hexadecanedioate, obtained from glutaric anhydride. Indeed, 6,11-diaza-5,12-dioxo-1,16-hexadecanedioate cyclizes and the product prevents polymerization and the formation of a poly(esteramide) polymer.

However, as glutaric and succinic acid monomers are inexpensive, polymers prepared from the latter would be of interest.

SUMMARY AND DETAILED DESCRIPTION

A goal of the present invention is to provide a polymer:
useful as an additive for improving heat resistance of a polymeric composition, and in particular of a polymeric composition comprising natural fibers, and/or
useful as a polymeric matrix of a polymeric composition having a good heat resistance. The increase in the heat resistance is associated with an increase in the melting point of the polymeric composition, measurable by methods known to one skilled in the art.

For this purpose, the invention in one aspect provides a compound of formula (I) which may be used as a starting product for preparing a poly(esteramide) polymer useful as an additive or as a polymeric matrix as defined above. Advantageously, the compound of formula (I), and the poly(esteramide) polymer obtained from said compound, may notably be prepared from glutaric or succinic acid or from their derivatives, unlike the known poly(esteramide) polymers.

Thus, according to a first object, the invention relates to a compound of the following formula (I):

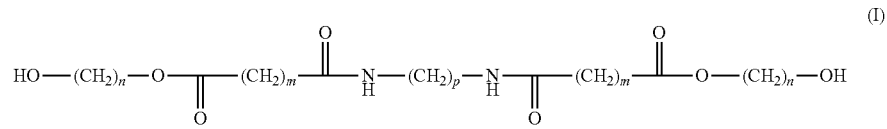

(I)

wherein n and p independently represent an integer from 2 to 12 and m independently represents an integer from 1 to 12. Preferably n and p independently represent an integer from 2 to 6 and/or m represents an integer from 1 to 4.

Generally, in the above formula (I), p and n are identical and independently represent an integer from 3 to 12 and m represents (n–2). Thus, if the compound of formula (I) is broken down into subunits as explained on the following diagram, each subunit has the same number of carbon atoms with the advantages described hereafter.

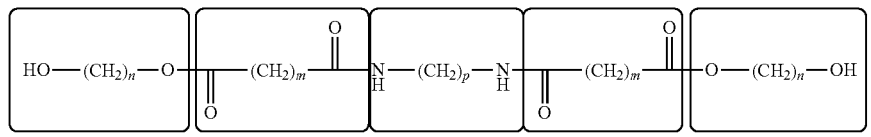

In an embodiment, in the above formula (I), m, n and p are even integers. The polymers (PEA) prepared from such compounds actually give the possibility of improving the heat resistance of polymeric compositions more efficiently.

In an embodiment, in the above formula (I) m represents 2 or 3. Preferably, n and p represent 4 and m represents 2. Thus, the compound of formula (I) is formed with three different subunits but having the same number of carbon atoms, said subunits stemming from succinic acid, 1,4-butanediol and 1,4-butanediamine units. According to another alternative, n and p represent 5 and m represents 3. Thus, the compound of formula (I) is formed with three different subunits but with the same number of carbon atoms, said subunits being derived from glutaric acid,1,5-pentanediol and 1,5-pentanediamine units.

According to a second object, the invention relates to a method for preparing a compound of formula (I) as defined above, comprising a step consisting of coupling a compound having the following formula (II):

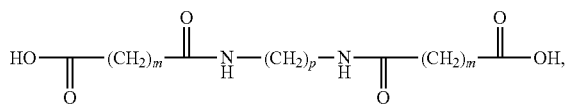
(II)

wherein m and p are as defined above,
with a dialcohol of the following formula (III):

 (III), wherein n is as defined above.

Typically, the method for preparing a compound of formula (I) comprises the steps:
a) bringing into contact a compound having the following formula (II):

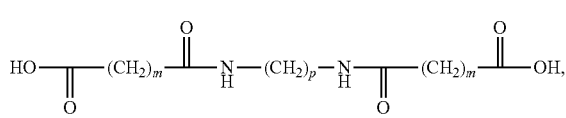
(II)

wherein m and p are as defined above,
with an excess of a dialcohol of the following formula (III):

 (III), wherein n is as defined above,
in order to obtain a reaction mixture,
b) heating the reaction mixture to a temperature from 50 to 200° C., the steps a) and b) being successive or simultaneous.

Step a) comprises the bringing of the compound of formula (II) into contact with an excess of dialcohol of formula (III). Typically, more than 5, or even more than 10 equivalents typically of the order of 14 equivalents of dialcohol of formula (III) relatively to the compound of formula (II), are used.

Step a) generally comprises the bringing of the compound formula (II) into contact with an excess of dialcohol of formula (III) in the presence of a catalyst, which promotes esterification occurring during step b). This catalyst may be an acid, a base or a metal and is typically an acid catalyst, for example paratoluenesulfonic acid.

The contacting of step a) is generally achieved in the absence of solvent.

During step b), a temperature above 50° C. is sufficient for the esterification reactions leading to the compound of formula (I) to occur, and the temperature is less than 200° C., preferably less than 150° C. in order to avoid degradation of the compound of formula (II). Step b) is generally carried out at atmospheric pressure.

Step b) is generally followed by a step for recovering the compound of formula (I). The purification methods for the compound are the purification methods usually applied by one skilled in the art (distillation, chromatography, re-precipitation ... ).

The dialcohols of formula (III) are advantageously commercial dialcohols, for example available at Sigma Aldrich®, Alfa Aesar®, VWR®, Brenntag®.

The compound of formula (II) may be synthesized according to methods known to one skilled in the art, for example by following the procedure described for the embodiment wherein m represents 2 and p represents 4 in US 2004/171518 (Example 3), by adapting this procedure starting from a diacid of the following formula (IV'):

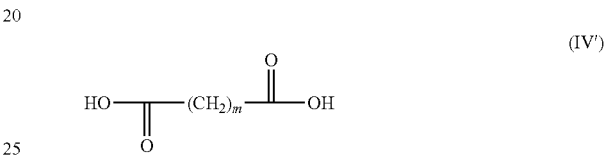
(IV')

or from the corresponding cyclic anhydride

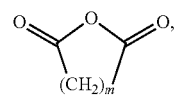

wherein m is as defined above,
and from a diamine of the following formula (V):

 (V), wherein p is as defined above.

The diacids of formula (IV') and their cyclic anhydride and the diamines of formula (V) are advantageously commercial compounds, for example available at Sigma Aldrich®, Alfa Aesar®, VWR®, UNIPEX®, DSM®.

Advantageously, the dialcohols of formula (III) and the compound of formula (II) may stem from renewable resources, as described in US 2009/0171037. Further, methods are presently developed and will shortly allow preparation of diamines of formula (V) from renewable resources. Thus, the compound of formula (II) would be advantageously synthesized from starting products stemming from renewable resources.

The compound of formula (I) according to the invention may be used as a precursor of a polymer, a so-called (PEA) polymer hereafter, useful as an additive for improving the heat resistance of a polymeric composition or as polymeric matrix of a polymeric composition presenting a good heat resistance.

According to a third object, the invention relates to a method for preparing a (PEA) polymer from the compound of formula (I). More specifically, the invention relates to a method for preparing a (PEA) polymer comprising a step consisting of heating to a temperature greater than or equal to the melting temperature of the compound of formula (I) and under reduced pressure, a compound of formula (I) in the presence of a catalyst for polymerizing the compound of formula (I).

In the sense of the present application, the polymer obtained by this method is designated by "(PEA) polymer".

The catalyst is preferably a metal catalyst, notably a metal salt or a derivative of a transition metal, the metal notably being titanium, zinc, aluminum, tin, germanium, hafnium, zirconium or antimony. Titanium complexes, preferably titanium alkoxides, such as $Ti(OEt)_4$, $Ti(OPr)_4$ or $Ti(OBu)_4$, are particularly suitable catalysts.

The polymerization is preferably carried out under reduced pressure, typically less than or equal to 0.8 bars, or even less than or equal to 0.1 bars, and by varying the temperature, more specifically by increasing it from an initial temperature above the melting temperature of the compound or formula (I): the polymerization is generally started at a temperature comprised between the melting temperature of the compound of formula (I) and 130° C., preferentially between 105 and 130° C., in particular at a temperature of the order of 120° C., and for a duration from 2 to 10 hours, typically of the order of 6 hours, and the temperature is then increased between 135 and 160° C., in particular to a temperature of the order of 150° C. for a duration from 2 to 10 hours, typically of the order of 6 hours, and finally the temperature is increased between 165 and 175° C., in particular to a temperature of the order of 170° C. for a duration from 1 to 5 hours, typically of the order of 2 hours.

The additives usually used for polymerization reactions may be added during the process. For example, it is possible to add chain extenders such as isocyanates, carbodiimides, epoxides, dianhydrides . . .

In a first embodiment, the (PEA) polymer self-polymerizes. Without wishing to be bound by a specific theory, it seems that in the presence of the catalyst and under the aforementioned temperature and pressure conditions, reactions of transesterifications or hydrolysis of at least one of the ester functions of the compound of formula (I) occur, generating a terminal carboxylic acid function which then forms an ester function with the terminal alcohol functions of the compound of formula (I) thereby causing polymerization of the compound of formula (I) in order to form the (PEA) polymer.

Generally, in this embodiment, the obtained (PEA) polymer is an alternating copolymer: it comprises an alternation between amide functions and ester functions. The obtained polymer typically has the following formula (VI):

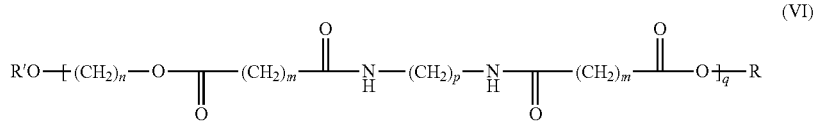
(VI)

wherein R represents H or a —$(CH_2)_n$—OH group and R' represents H or a —(CO)—$(CH_2)_m$—COOH group, n, m and p are as defined above and q is an integer depending on the degree of polymerization.

The obtained (PEA) polymer is generally semi-crystalline.

In a second embodiment, the compound of formula (I) is brought into contact under the aforementioned temperature and pressure conditions with a compound of the following formula (IV):

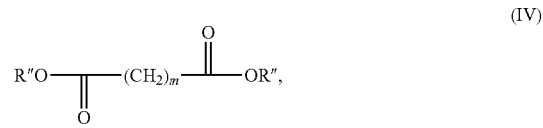
(IV)

wherein m is as defined above and R" represents H or an alkyl with 1 to 5 carbon atoms, preferably a methyl or ethyl.

The compound of formula (I) and the compound of formula (IV) are typically used in equimolar amounts.

In this embodiment, without wishing to be bound by a specific theory, it seems that during the polymerization, the terminal alcohol functions of the compound of formula (I) reacts with the carboxylic acid functions of the compound of formula (IV) and/or with the carboxylic acid functions generated by hydrolysis of the ester function of the compound of formula (I), as explained above.

Generally, in this embodiment, the obtained (PEA) polymer is an alternating copolymer: it comprises an alternation between amide functions and ester functions.

The obtained polymer typically as the following formula (VII):

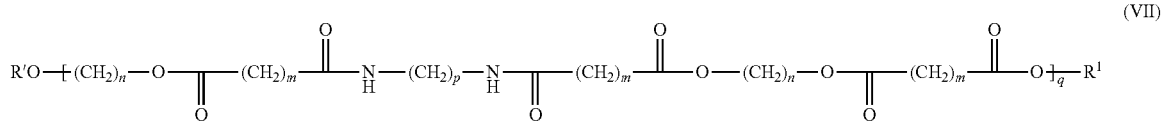
(VII)

wherein $R^1$ represents R" or a —$(CH_2)_n$—OH group and R' represents H or a —(CO)—$(CH_2)_m$—COOR" group, n, m and p are as defined above and q is an integer depending on the degree of polymerization.

The obtained (PEA) polymer is generally semi-crystalline.

In a third embodiment, the compound of formula (I) is brought into contact under the aforementioned temperature and pressure conditions both with a compound of formula (IV) as defined above and with a compound of the following formula (III):

HO—$(CH_2)_n$—OH  (III), wherein n is as defined above.

In this embodiment, without wishing to be bound by a specific theory, it seems that during the polymerization, the terminal alcohol functions of the compound of formula (I)

and those of the compound of formula (III) react with the carboxylic acid functions of the compound of formula (IV) and/or with the carboxylic acid functions generated by cleavage of the ester function of the compound of formula (I), as explained above.

The polymer obtained in this embodiment is typically a random polymer.

According to a fourth object, the invention relates to the (PEA) polymer obtainable according to the method described above.

The polymers (PEA) obtainable by the method described above with a compound of formula (I) wherein:
  m, n and p are even integers, or
  m represents 2 or 3, and preferably:
    n and p represent 4 and m represents 2, or
    n and p represent 5 and m represent 3, are preferred.

The (PEA) polymer obtainable by the method typically has a weight average molecular weight comprised between 1,000 and 100,000 g/mol, preferably greater than 10,000 g/mol. Such polymers (PEA) actually allow more efficient improvement of the heat resistance of polymeric compositions.

The (PEA) may be used as a polymeric matrix of a polymeric composition having a good heat resistance, typically which withstands temperatures above 120° C.

The (PEA) polymer is also used for as an additive in a polymeric composition for improving the heat resistance thereof. The invention also relates to the use of the (PEA) polymer according to the invention for improving the heat resistance of a composition comprising a polymer (P), in particular of a composition comprising a polymer (P) and natural fibers. Further, the (PEA) may be used as a compatibilizing agent between semi-polar and polar polymeric matrices, typically between polyesters and polyamides, starch . . . , with polar fillers (cloisite, montmorillonite . . . ) and polar reinforcements (hemp, flax, sisal, wood flour . . . ).

Thus, according to a fifth object, the invention relates to a composition comprising:
  a (PEA) polymer according to the invention, as defined above,
  optionally at least one other polymer (P), and
  optionally natural fibers.

When the composition comprises a polymer (P), the (PEA) polymer is an additive of a composition. When the composition is without any polymer (P), the (PEA) polymer is the polymeric matrix of the composition. In both embodiments, the obtained composition has good heat resistance, i.e. typically it withstands temperatures above 120° C.

Preferably, the polymer (P) is a polyamide, polyester, polyamide/polyester copolymer or a mixture thereof (polyamide-polyester blend). The polyester is typically an aliphatic polyester, notably poly(butylene succinate) (PBS). The (PEA) polymer actually has a structure close to these polymers and is therefore easily dispersible in the latter, and thus a homogeneous composition may advantageously be obtained.

In the embodiment described above wherein p and n are identical and m represents (n-2), each subunit of the compound of formula (I), and therefore of the (PEA) polymer has the same number of carbon atoms, and incorporation of the (PEA) polymer into the crystalline lattice of the polymer (P) is promoted.

The composition optionally comprises natural fibers. The natural fibers are preferably:
  fibers of plant origin, notably selected from the group formed by cotton, flax, hemp, Manila hemp or abaca, banana tree, coconut, jute, ramie, raffia, sisal, broom, bamboo, miscanthus, kenaf, coprah, agave, sorghum, switch-grass and wood, and/or
  fibers of animal origin, notably selected from the group formed by wool, alpaca fleece, mohair, cashmere, angora and silk.

With these fibers it is notably possible to improve the thermomechanical performances, notably the stiffness and sometimes to lighten the obtained composition. The preferred fibers are hemp, flax, sisal, preferably hemp.

The composition typically comprises from 10 to 40%, notably from 20 to 35%, preferably from 25 to 30% by weight of fibers.

The composition may further comprise additives usually used in polymer compositions, such as:
  an impact resistance additive (for example acrylic copolymers, elastomers), and/or
  an anti-hydrolysis additive (for example carbodiimides, epoxides), and/or
  a fluidifying agent (for example oligomers, lubricants, plasticizers) and/or
  an antifungal agent, and/or
  anti-oxidants (phosphoric, phenolic . . . ), and/or
  fillers (talcum, calcium carbonate . . . ), and/or
  nanofillers (montmorillonite, cloisite . . . ), and/or
  an anti-UV agent (phenolic hindered amines . . . ), and/or
  a coloring agent or a pigment, and/or
  a flame-retardant, and/or
  a compatibilizing agent (maleic anhydride, silanes . . . ).

This composition may be used for preparing plastic articles, notably vehicle parts and typically for automobile parts where thermal and mechanical constraints are important and of particular interest. Thus, according to a sixth object, the invention relates to plastic articles, notably vehicle parts, such as automobile parts, comprising the composition according to the invention. The plastic article may be, as an example, an interior trim of an automobile such as instrument panel. The plastic article may, as known by a man skilled in the art, be used without covering or with a covering layer.

The plastic articles are notably obtainable with usual methods for transforming plastic materials, typically by injection, back injection, thermocompression, thermoforming, preferably by injection.

The invention will be better understood considering the examples hereafter.

EXAMPLE 1

Synthesis of a Compound of Formula (I')
(Corresponding to a Compound of Formula (I) in which n and p Represent 4 and m Represents 2)

The compound of the following formula (II'):

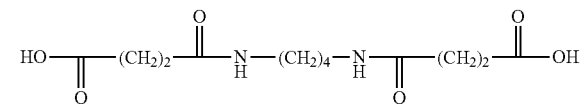

(corresponding to a compound of formula (II) wherein p represents 4 and m represents 2) was synthesized by following the procedure described in Example 3 of US 2004/0171518.

10 g (0.035 mol) of the compound of formula (II') and 45 g of 1,4-butanediol (0.5 mol) (corresponding to a compound of formula (III) wherein n represents 4) (a 1,4-butanediol/formula (II') compound ratio of about 95/5) were mixed, and then 0.0035 mol (10% molar of paratoluene-sulfonic acid relatively to the molarity of the compound of formula (II')) were added with stirring, and the obtained mixture was heated in an oil bath at 100° C. for 4 hours with an open neck.

The excessively used 1,4-butanediol may be recovered by washing the medium with acetonitrile in which it is soluble, filtration of the insoluble compound of formula (I'). The 1,4-butanediol may thus be recycled.

The yield in an isolated compound of formula (I') is greater than 30%.

The compound of the following formula (I') is obtained as a solid:

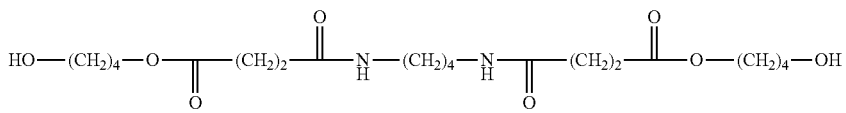

Its melting temperature is 105° C. and its degradation temperature (mass loss) by thermogravimetric analysis (ATG) is 200° C., which is advantageously much greater than the temperatures usually used during the synthesis of polymers, in particular of polyesters, by extrusion. HRMS (MALDI-TOF): m/z: 455.2363.

EXAMPLE 2

Preparation of a (PEA) Polymer from the Compound of Formula (I') of Example 1 a) By Self Polymerization of the Compound of Formula (I')

The polymerization of the compound of formula (I') was conducted in the presence of a catalyst $Ti(OBu)_4$ at 0.2% mol relatively to the total molarity in a toluene solvent under reduced pressure (pressure below 0.1 bars):
at a temperature of 120° C. for 6 hours, and then
at a temperature of 150° C. for 6 hours, and then
at a temperature of 170° C. for 2 hours.

The obtained (PEA) polymer is an alternating copolymer with a weight average molecular weight Mw (as measured by MALDI-TOF) of 1,340 g/mol: it comprises an alternation between amide functions and ester functions.

The obtained (PEA) polymer has a melting point ranging from 141° C. to 172° C. depending on the crystallization conditions (measured by differential scanning calorimetry on an apparatus of the DSC 2920 Modulated DSC TA instrument type, with temperatures cooled at a rate of 20° C./min (Tm=141° C.) down to 150° C. annealings for 1 h (Tm=170° C.)).

A poly(butylene succinate) has a melting point of 106° C. An increase in the melting point by at least 35° C. is therefore observed.

The formed (PEA) polymer is a derivative of poly(butylene succinate) into which amide functions have been introduced. By introducing (PEA) into a polymeric composition comprising poly(butylene succinate), it is possible to improve the heat resistance of said composition.

b) By Polymerization of the Compound of Formula (I') in the Presence of Succinic Acid Polymerization of the compound of formula (I') whilst conducted in the presence of succinic acid (an equimolar mixture of the compound of formula (I') and of succinic acid) and of 0.2% mols of catalyst $Ti(OBu)_4$ under reduced pressure:
at a temperature of 120° C. for 6 hours, at a pressure below 0.8 bars, and then
at a temperature of 150° C. for 6 hours, at a pressure below 0.1 bars and then
at a temperature of 170° C. for 2 hours, at a pressure below 0.1 bars.

A (PEA) polymer is produced with an Mw (by MALDI TOF) of 1,665 g/mol having a melting point ranging from 115° C. to 140° C. depending on the crystallization conditions (as measured by differential scanning calorimetry (DSC)). The obtained (PEA) polymer is an alternating co-polymer: it comprises an alternation between the amide functions and the ester functions.

c) By Polymerization of the Compound of Formula (I') in the Presence of Succinic Acid and of 1,4-butanediol Tests were conducted with:
1 mole of compound of formula (I')+3 moles succinic acid (SA)+2 moles of 1,4-butanediol, or
1 mole of compound of formula (I')+7 moles of succinic acid (SA)+6 moles of 1,4-butanediol.

Under these conditions, a non-crystalline and random (PEA) polymer was obtained.

The invention claimed is:

1. A compound of the following formula (I):

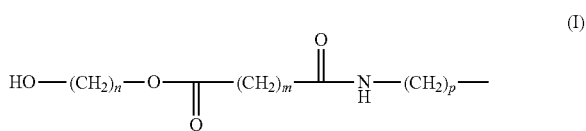

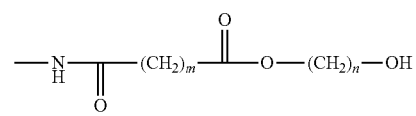

wherein n and p are identical and independently represent an integer from 3 to 12 and m represents (n−2).

2. The compound according to claim 1 wherein n, m and p are even integers.

3. The compound according to claim 1, wherein m represents 2 or 3.

4. A method for preparing a compound according to claim 1, comprising a step consisting of coupling a compound having the following formula (II):

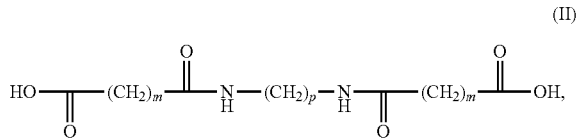

wherein m and p are as defined in claim 1,
with a dialcohol of the following formula (III):

wherein n is as defined in claim 1.

5. A method for preparing a (PEA) polymer comprising a step consisting of heating to a temperature greater than or equal to the melting temperature of the compound of formula (I) and under reduced pressure, a compound of formula (I) according to claim 1, in the presence of a catalyst, in order to polymerize said compound of formula (I).

6. The method for preparing a (PEA) polymer according to claim 5, wherein the compound of formula (I) is brought into contact with a compound of the following formula (IV):

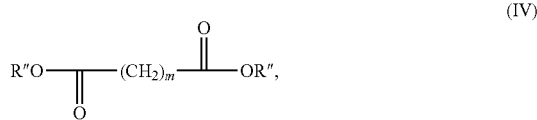

wherein n is as defined in claim 1 and R″ represents H or an alkyl with 1 to 5 carbon atoms.

7. The method for preparing a (PEA) polymer according to claim 5, wherein the compound of formula (I) is the compound according to claim 4.

8. A (PEA) polymer comprising subunits derived from succinic acid, 1,4-butanediol and 1,4-butanediamine and being obtainable by a method comprising a step consisting of heating a compound of formula (I) according to claim 1 wherein n and p represent 4 and m represents 2 to a temperature greater than or equal to the melting temperature of said compound of formula (I) and under reduced pressure, in the presence of a catalyst, in order to polymerize said compound of formula (I).

9. A method for improving the heat resistance of a composition, comprising the step of adding to said composition a (PEA) polymer according to claim 8.

10. A composition comprising:
a (PEA) polymer according to claim 8.

11. A composition according to claim 10, comprising at least one other polymer (P), and/or natural fibers.

12. The method for preparing a (PEA) polymer according to claim 6, wherein the compound of formula (I) is brought into contact with a compound of the following formula (III):

wherein n is as defined in claim 1.

13. A plastic article comprising a composition according to claim 11.

14. A (PEA) polymer comprising subunits derived from glutaric acid, 1,5-pentanediol and 1,5-pentanediamine and being obtainable by a method comprising a step consisting of heating a compound of formula (I) according to claim 1 wherein n and p represent 5 and m represents 3 to a temperature greater than or equal to the melting temperature of said compound of formula (I) and under reduced pressure, in the presence of a catalyst, in order to polymerize said compound of formula (I).

15. A method for improving the heat resistance of a composition, comprising the step of adding to said composition a (PEA) polymer according to claim 14.

16. A composition comprising a (PEA) polymer according to claim 14.

17. A composition according to claim 16, comprising at least one other polymer (P), and/or natural fibers.

18. A plastic article comprising a composition according to claim 17.

* * * * *